United States Patent [19]

Lohse

[11] Patent Number: 4,520,829

[45] Date of Patent: Jun. 4, 1985

[54] METHOD OF TAKING ANGIOGRAPHS

[75] Inventor: Karl-Heinz Lohse, Im Bans 20a, 2080 Pinneberg, Fed. Rep. of Germany

[73] Assignee: Karl-Heinz Lohse, Pinneberg, Fed. Rep. of Germany

[21] Appl. No.: 430,496

[22] Filed: Sep. 30, 1982

[30] Foreign Application Priority Data

Feb. 5, 1982 [DE] Fed. Rep. of Germany ....... 3204037

[51] Int. Cl.$^3$ .............................................. A61B 6/00
[52] U.S. Cl. .................................................... 128/654
[58] Field of Search .............................. 128/653–654; 378/62

[56] References Cited

U.S. PATENT DOCUMENTS

| | | | |
|---|---|---|---|
| 2,379,814 | 7/1945 | McFarland | 378/62 |
| 3,121,792 | 2/1964 | Mittelstaedt | 378/62 X |
| 3,231,737 | 1/1966 | Mittelstaedt | 378/62 X |
| 4,322,619 | 3/1982 | Nelson et al. | 378/62 |

FOREIGN PATENT DOCUMENTS 2828854 1/1980 Fed. Rep. of Germany ........ 378/62

OTHER PUBLICATIONS

Mardix, S., "Radiographs in Relief", Materials Evaluation, vol. 4, #5, May 1976, pp. 97–102.

*Primary Examiner*—Kyle L. Howell
*Assistant Examiner*—Francis J. Jaworski
*Attorney, Agent, or Firm*—Lilling & Greenspan

[57] ABSTRACT

Angiographic process utilizing contrast mediums for the roentgenographic representation of living organ vessels, especially human, wherein a blank photograph is made of a vascular region to be visualized, a contrast medium is infused into said vascular region, a photograph of the same region is produced after a given time interval, for example 0.5 seconds, and a visual image is produced by photographic subtraction of the two pictures, whereby the quantity of the contrast medium and the X-ray dose used to produce the pictures are reduced by photographically equivalent factors to such an extent that the desired information lies in a density range (blackening range) unsuited to direct observation, and whereby in the process of photographic subtraction the density range containing the information is extracted and transposed onto a visual density range suitable for direct observation of the image.

7 Claims, No Drawings

METHOD OF TAKING ANGIOGRAPHS

BACKGROUND OF THE INVENTION

1. Field of the Invention

The invention concerns an angiographic process.

2. Description of the Prior Art

This process is customary in angiographic practice and affords the advantage that the vascular structures made recognizable in the viewing picture by the contrast medium are in sharp relief. In theory, the entire residual picture content could vanish; in practice, however, weak relief-like indications of other organ structures or bones persist on account of unavoidable differences in the conditions of photography, especially on account of the inevitable movements of the living vascular region. This facilitates orientation in studying the picture.

After instilling the contrast medium, a whole series of pictures is mostly taken at given time intervals, for example every 0.5 seconds, which are all processed into viewing pictures by photographic subtraction of a blank photograph or reference radiograph, so that the propagation of the contrast medium and possible obstructions in the vascular system may be recognized therein. Since this involves taking at least two, but usually many more pictures, there is considerable radiation exposure of the organism to be examined. This is particularly so when overexposure is practiced, as is often the case, to ensure obtaining usable photographs. Yet, details of diagnostic interest are often difficult to recognize, if at all, in the viewing picture, because of inadequate density differentials (differences of blackening) that are depicted.

SUMMARY OF THE INVENTION

Hence, the invention aims to create an angiographic process affording high-quality viewing pictures with considerably lower radiation doses.

According to the invention, this aim is achieved by an angiographic process conforming to claim 1.

According to the invention process, the density range may be readily tranaposed by 2 to 4 units, in other words the radiation dose utilized for the picture may be reduced by a factor of $10^2$ to $10^4$. The reduction of the contrast medium is also considerable. Allowing for the normally high price of conventional contrast mediums, this results in considerable cost savings; beyond that, the exposure of the organism to contrast mediums is sharply reduced.

DETAILED DESCRIPTION

Manifestly, in the invented process the density range unsuited to direct observation should not be chosen too close to zero, as this reaches down to the area of inception of the blackening curve of photographc layers where the usability of photographic processes finds its natural limit. Conversely, it is entirely feasible to select areas of very low density (blackening), corresponding to an appreciable reduction of the exposure time by several orders of magnitude. In the simplest case, the density range unsuited to direct observations is chosen at about 0.2 to 1.5. This already reduces exposure time to about one-tenth.

It is particularly advantageous if the density range unsuited to direct observation is transposed onto a larger density range for viewing; this is readily feasible by the use of hard photographic material.

The process according to the invention requires only simple steps, readily performed with a high degree of precision and reproducibility, which are by themselves all known in photographic techniques. The invented process is particularly simple if the photographs are the usual transparencies and if in producing the viewing picture, a reverse slide of the blank or reference radiograph picture is produced by known methods of photographic subtraction, and the reverse slide is superimposed in proper register on the photographic slide to be copied into the viewing picture, changing if need be the scale of the illustration. This is consistent with the conventional method of operations, obviating the need for any new operational training practice. It can be readily appreciated that the described operating sequences can be without further ado performed mechanically and automatically, so that no fundamental difficulties arise in designing facilities wherein the production of the reverse slide, the superimposition of the two slides and the production of the viewing picture may proceed mechanically in an automatic cycle. Such an automatic operating cycle is naturally of particular advantage. This is the more true as it is readily possible to standardize angiographic processes to certain frequently examined vascular regions, for example the heart, brain, gallbladder and the like. Thus, for each such region essentially uniform recording conditions would prevail in all examinations, so that it would be very easy by appropriate trial to select process parameters (exposure time, photographic development constants) such as would ensure optimum results for a whole series of examinations.

Appropriately, to produce the just mentioned reversal slides, one would use photographic material with a contrast of 1 ($\gamma=1$), whereas material of sharper contrast would be used for the production of the viewing picture; in this manner, it is feasible to transpose a relatively narrow blackening range, for example 0.2 to 1.5 wherein the desired information is contained, onto a suitably larger blackening range, for example 0.5 to 2.5, particularly advantageous to direct observation. Conversely, for the production of reverse slides, a contrast of 1 is required so that the masking of the picture slide with the reverse slide may extinguish as much as possible the structures that are not of interest. It goes without saying that provision can be made for a faint visualization of these structures, by utilizing in the production of reverse slides a material with a contrast slightly different from 1, and/or by deliberate slight deviation from a perfect register of the two slides. Such techniques are by themselves already known.

Preferably, the photographic material of sharper contrast is material with a contrast index in the range of about 3 to 8. In most cases, a contrast of 3 will prove satisfactory. Sharper contrasts require commensurately higher accuracy in exposure and processing of the photographic material.

The enhanced contrast resulting from the use of photographic material of sharper contrast in the production of viewing pictures makes it possible to visualize structures not recognizable in ordinary photographs on account of limited density differentials. In this way it is, for example, possible to gain dependable information on the condition of the vascular walls. It goes without saying that for these and similar special tasks, the contrast enhancement may be greater than would be selected for the depiction of photographically more differentiated structures. Thus for example one can, to good advantage, at first photograph the vessels with limited contrast expansion, and then produce further pictures of greater contrast expansion, suitable to pinpoint specific fine structures. In any event, the extracted and contrast-enhanced density range may be varied by known methods, varying the exposure in the production of the viewing picture.

I claim:

1. Angiographic process utilizing contrast mediums for the roentgenographic representation of living organ vessels, especially human, wherein a reference radiograph is made of a vascular region to be visualized, a contrast medium is infused into said vascular region, a photograph of the same region is produced after a given time interval, for example 0.5 seconds and a visual image is produced by photographic substraction of the two pictures, wherein the process further comprises the steps of reducing the quantity of the contrast medium and the x-ray dose used to produce the pictures by photographically equivalent factors to such an extent that the desired information lies in a density range (blackening range) unsuited to direct observation, and extracting and transposing in the process of photographic subtraction, the density range containing the information into a visual density range suitable for direct observation of the image.

2. Process according to claim 1, wherein the density range unsuited to direct observation is chosen at approximately 0.2 to 1.5.

3. Process according to claim 1 or 2, wherein the unsuitable density range is transposed in to a larger visual density range.

4. Process according to claim 1, wherein the photographs are slides, wherein for the purpose of producing a visual picture a reversal slide is made of the reference radiograph by a known method of photograhic subtraction, and that the reverse slide and the photographic slide are superimposed in proper register and copied into the visual picture, changing if need be the scale of the image.

5. Process according to claim 4, wherein the production of the reverse slide, the superimposition of the two slides and the production of the visual picture are done mechanically in automatic sequence.

6. Process according to claim 1, wherein the photographs are slides and the photographic material used for the production of the reversal slide has a contrast index of 1, while for the production of the visual image material of steeper contrast is used.

7. Process according to claim 6, wherein a material with a contrast index in the range of about 3 to 8 is used as material of steeper contrast.

* * * * *

UNITED STATES PATENT AND TRADEMARK OFFICE
CERTIFICATE OF CORRECTION

PATENT NO. : 4,520,829

DATED : June 4, 1985

INVENTOR(S) : Karl-Heinz Lohse

It is certified that error appears in the above-identified patent and that said Letters Patent is hereby corrected as shown below:

Change Assignee data to:

[73] Assignee: STB Strahlentechnische Bilddiagnostik Heinz Fleck,

Federal Republic of Germany

Signed and Sealed this

Fourth Day of November, 1986

[SEAL]

*Attest:*

DONALD J. QUIGG

*Attesting Officer*  *Commissioner of Patents and Trademarks*